United States Patent
Hara et al.

(10) Patent No.: US 8,957,136 B2
(45) Date of Patent: Feb. 17, 2015

(54) EPOXYSILICONE CONDENSATE, CURABLE COMPOSITION COMPRISING CONDENSATE, AND CURED PRODUCT THEREOF

(75) Inventors: Masanao Hara, Minato-ku (JP); Hiroshi Uchida, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 186 days.

(21) Appl. No.: 13/814,573

(22) PCT Filed: Aug. 8, 2011

(86) PCT No.: PCT/JP2011/068069
§ 371 (c)(1),
(2), (4) Date: Feb. 6, 2013

(87) PCT Pub. No.: WO2012/020730
PCT Pub. Date: Feb. 16, 2012

(65) Prior Publication Data
US 2013/0137795 A1    May 30, 2013

(30) Foreign Application Priority Data
Aug. 11, 2010    (JP) .................................. 2010-180178

(51) Int. Cl.
*C07F 7/08*    (2006.01)
*C08G 77/14*    (2006.01)
(Continued)

(52) U.S. Cl.
CPC ............. *C07F 7/0812* (2013.01); *C07F 7/1836* (2013.01); *H01L 23/296* (2013.01);
(Continued)

(58) Field of Classification Search
None
See application file for complete search history.

(56) References Cited

U.S. PATENT DOCUMENTS

| 7,880,018 B2 * | 2/2011 | Sasaki et al. .................. 548/406 |
| 2004/0116640 A1 | 6/2004 | Miyoshi |

(Continued)

FOREIGN PATENT DOCUMENTS

| JP | 58-222160 A | 12/1983 |
| JP | 2004-155865 A | 6/2004 |

(Continued)

OTHER PUBLICATIONS

International Search Report of PCT/JP2011/068069 dated Nov. 8, 2011.

*Primary Examiner* — Robert S Loewe
(74) *Attorney, Agent, or Firm* — Sughrue Mion, PLLC

(57) ABSTRACT

There is provided an epoxy group-containing silicone condensate that yields cured products with excellent transparency, thermal resistance and gas barrier properties. An epoxysilicone condensate which is the product of hydrolytic condensation of an epoxy group-containing alkoxysilane compound represented by formula (1):

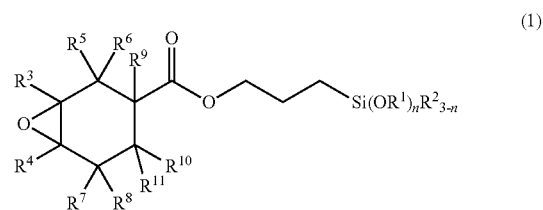

(1)

and an alkoxysilane compound represented by formula (2):

$$Si(OR^{12})_m R^{13}_{4-m}$$ (2)

wherein when the number of moles of the epoxy group-containing alkoxysilane compound (1) is x and the number of moles of the alkoxysilane compound (2) is y, $0.2 \leq my/nx \leq 0.7$, a curable composition comprising the condensate, and a cured product of the composition.

10 Claims, 4 Drawing Sheets

(51) Int. Cl.
*C07F 7/18* (2006.01)
*H01L 23/29* (2006.01)
*C08L 83/06* (2006.01)
*G02B 1/04* (2006.01)
*C08G 59/30* (2006.01)
*H01L 33/56* (2010.01)

(52) U.S. Cl.
CPC .................. *C08L 83/06* (2013.01); *G02B 1/04* (2013.01); *H01L 33/56* (2013.01); *C08G 59/306* (2013.01); *G02B 1/041* (2013.01); *C08G 77/14* (2013.01)
USPC .............................. 523/400; 549/215; 528/41

(56) References Cited

U.S. PATENT DOCUMENTS

2009/0256287 A1* 10/2009 Fu et al. .................. 264/447

| | | | |
|---|---|---|---|
| 2010/0197936 A1 | 8/2010 | Sasaki et al. | |
| 2010/0258983 A1 | 10/2010 | Morinaka et al. | |
| 2011/0021788 A1 | 1/2011 | Arai et al. | |

FOREIGN PATENT DOCUMENTS

| | | |
|---|---|---|
| JP | 2004-186168 A | 7/2004 |
| JP | 2004-221308 A | 8/2004 |
| JP | 2008-248170 A | 10/2008 |
| JP | 2010-024229 A | 2/2010 |
| JP | 2010-106199 A | 5/2010 |
| JP | 2010-111811 A | 5/2010 |
| WO | 2008/020637 A1 | 2/2008 |
| WO | 2009/060862 A1 | 5/2009 |
| WO | 2009/119469 A1 | 10/2009 |

\* cited by examiner

EPOXYSILICONE CONDENSATE, CURABLE COMPOSITION COMPRISING CONDENSATE, AND CURED PRODUCT THEREOF

CROSS REFERENCE TO RELATED APPLICATIONS

This application is a National Stage of International Application No. PCT/JP2011/068069 filed Aug. 8, 2011, the contents of which are incorporated herein by reference in their entirety.

TECHNICAL FIELD

The present invention relates to an epoxysilicone condensate with an alicyclic epoxy group in the molecule, a curable composition comprising the condensate, and a cured product thereof.

BACKGROUND ART

Epoxy resins have been commonly used in the past as encapsulants for light emitting diode (LED) elements and semiconductor chips, from the viewpoint of adhesion with the substrates on which such parts are mounted, as well as toughness and gas barrier properties.

When epoxy resins are used as encapsulants, however, the thermal resistance and light resistance of such resins being inadequate, coloration of the encapsulant is observed with blue and white LEDs that have high heat release and light energy, and thus the performance of such LED elements is significantly reduced.

Much research is therefore being conducted on the use of silicone resins with excellent thermal resistance and light resistance, as LED encapsulants (see Patent Documents 1 and 2, for example). However, since silicone resins have poor adhesion to metal surfaces of wiring sections and with organic resins that are used as reflector plates (reflectors), detachment of encapsulating resins takes place with long-term use when silicone resins are used as LED encapsulating resins.

In order to improve the drawbacks of silicone resins, research has been carried out on epoxysilicone resins that have epoxy groups as substituents in the repeating units of the siloxane backbone (Patent Documents 3 and 4, for example). Such resins are anticipated to exhibit the thermal resistance, light resistance and transparency of silicone resins, in combination with the hardness, strength and adhesion of epoxy resins.

Patent Document 3 discloses a silicone composition comprising an epoxy group and an alicyclic hydrocarbon group as substituents on silicon, and the method accomplishes synthesis by introduction of substituents by hydrosilylation in a siloxane copolymer comprising Si—H groups. Since this method results in unreacted Si—H groups remaining in the composition in many cases, gas bubbles can potentially be included in the cured product due to hydrogen gas generated by hydrolysis of the Si—H groups.

Patent Document 4 discloses a method for producing a polyfunctional epoxysilicone resin wherein a trialkoxysilane compound comprising a glycidyl group or an epoxycyclohexyl group is subjected to high molecularization with water and an acidic catalyst or basic catalyst, and then a monoalkoxysilane is used as an end-capping agent for end capping of the residual alkoxy and silanol groups. While a curable resin composition with high transparency, high hardness, high light resistance and a low shrinkage rate can be obtained by this method, the low proportion of silicone sites in the resin composition can result in thermal resistance problems that are drawbacks of the epoxy resin.

Another problem faced with silicone resins in recent years is high gas permeability. The resulting problems that are encountered include deterioration of inorganic phosphors in LEDs due to moisture passing through the encapsulating resin, and oxidative degradation of the silver plating surfaces of substrate wirings due to oxygen. In this regard, Patent Documents 3 and 4 describe improving thermal resistance, light resistance, transparency, hardness and shrinkage rate by using the resins set forth therein, but they do not mention improvement in gas barrier properties.

Patent Document 5 also discloses a novel epoxy compound useful as a raw material for encapsulants, molding materials, casting materials, laminating materials, composite materials, adhesives and powder coatings for electric, electronic and optical parts, as well as silane coupling agents and modified silicone. However, it does not mention epoxysilicone condensates of the aforementioned epoxy compounds.

PRIOR ART

Patent Document

[Patent Document 1] Japanese Unexamined Patent Publication No. 2004-221308

[Patent Document 2] Japanese Unexamined Patent Publication No. 2004-186168

[Patent Document 3] Japanese Unexamined Patent Publication No. 2004-155865

[Patent Document 4] Japanese Unexamined Patent Publication No. 2008-248170

[Patent Document 5] International Patent Publication No. WO2008/020637

SUMMARY OF THE INVENTION

Problems to be Solved by the Invention

In light of the problems mentioned above, it is an object of the present invention to provide an epoxy group-containing silicone condensate that can yield cured products with excellent transparency, thermal resistance and gas barrier properties.

Means for Solving the Problems

The present inventors have conducted much diligent research with the aim of solving the problems mentioned above, and as a result have found that the problems can be solved by the cured product of a curable composition comprising an epoxysilicone condensate which is obtained by hydrolytic condensation of an epoxy group-containing alkoxysilane compound represented by formula (1) below, together with an alkoxysilane compound represented by formula (2) below, in the presence of an acidic catalyst or a basic catalyst. Specifically, the invention includes the following.

[1] An epoxysilicone condensate which is the product of hydrolytic condensation of an epoxy group-containing alkoxysilane compound represented by the following formula (1):

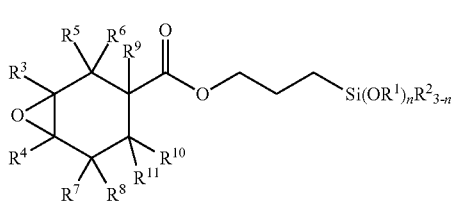  (1)

(wherein $R^1$ and $R^2$ each independently represent a C1-5 alkyl group, $R^3$ to $R^{11}$ each independently represent hydrogen or a C1-6 alkyl or C3-12 trialkylsilyl group, and n is an integer of 1 to 3, and $R^5$ or $R^6$, and $R^7$ or $R^8$, may optionally be linked together to form a ring), and an alkoxysilane compound represented by the following formula (2):

  (2)

(wherein $R^{12}$ and $R^{13}$ each independently represent a C1-5 alkyl group, and m is an integer of 1 to 3),
wherein when the number of moles of the epoxy group-containing alkoxysilane compound (1) is x and the number of moles of the alkoxysilane compound (2) is y, $0.2 \leq my/nx \leq 0.7$.

[2] The epoxysilicone condensate according to [1] above, wherein $R^3$ to $R^{11}$ in formula (1) are all hydrogen.

[3] A curable composition comprising the epoxysilicone condensate according to [1] or [2] above.

[4] A cured product of the curable composition according to [3] above.

[5] An optical element comprising the cured product according to [4] above as an encapsulant.

[6] An electronic component comprising the cured product according to [4] above as an encapsulant.

Effect of the Invention

A cured product of the curable composition comprising an epoxy group-containing silicone condensate of the invention has excellent transparency, thermal (yellowing) resistance and gas barrier properties, and is therefore useful as a raw material for an optical material, such as a plastic lens, or as an encapsulant for an optical element, such as a light emitting diode (LED), and an electronic component, such as a semiconductor chip.

MODE FOR CARRYING OUT THE INVENTION

Figure 1:
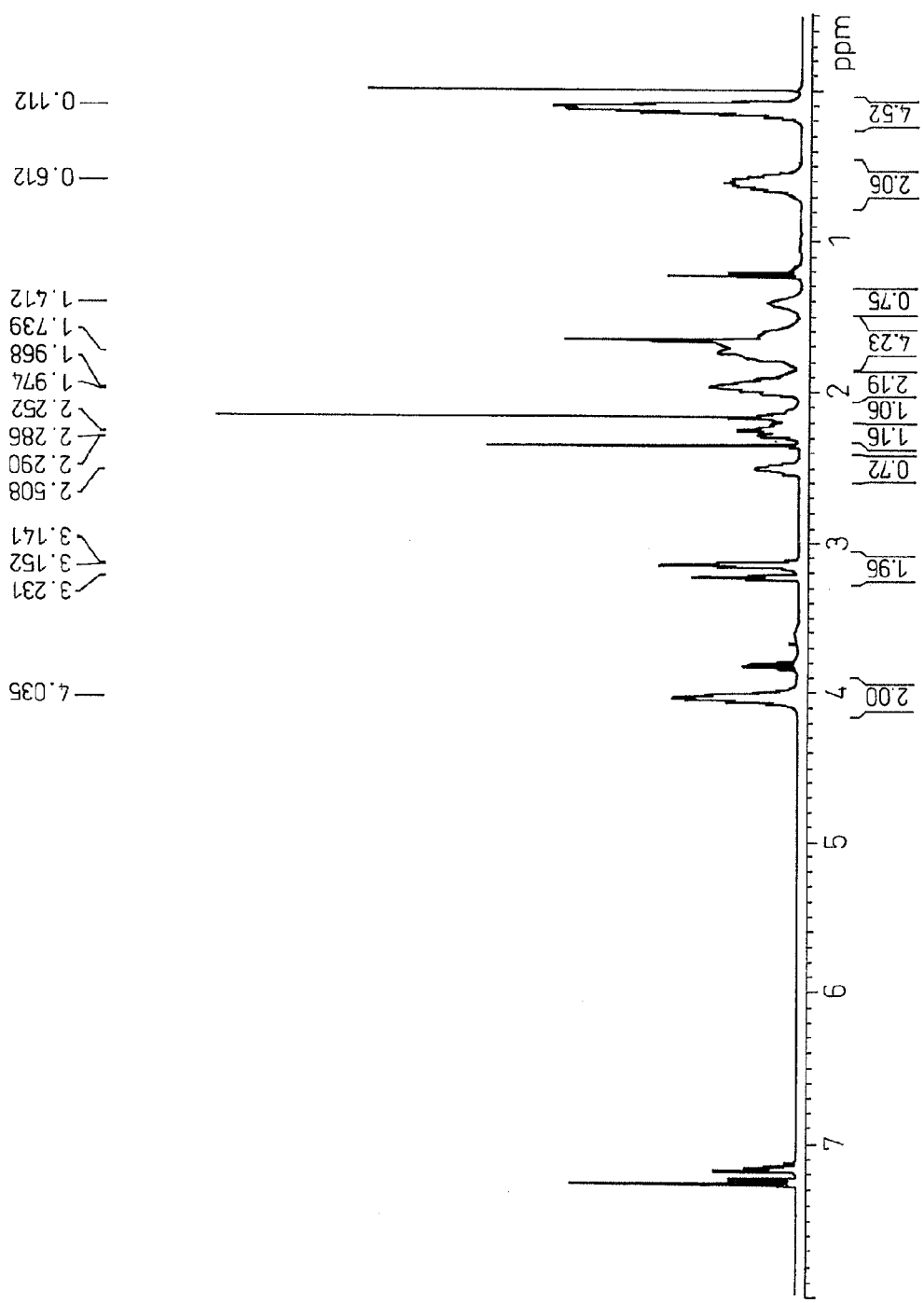
FIG. 1 shows an ¹H-NMR spectrum for the epoxysilicone condensate obtained in Example 1.

The invention will now be explained in greater detail.

The epoxysilicone condensate of the invention is obtained by mixing an epoxy group-containing alkoxysilane compound represented by the following formula (1):

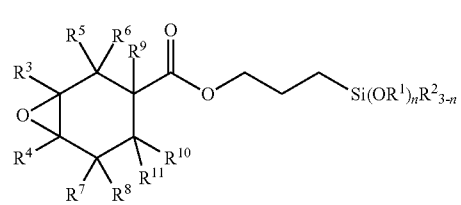  (1)

(wherein $R^1$ and $R^2$ each independently represent a C1-5 alkyl group, $R^3$ to $R^{11}$ each independently represent hydrogen or a C1-6 alkyl or C3-12 trialkylsilyl group, and n is an integer of 1 to 3, and $R^5$ or $R^6$, and $R^7$ or $R^8$, may optionally be linked together to form a ring), and an alkoxysilane compound represented by the following formula (2):

  (2)

(wherein $R^{12}$ and $R^{13}$ each independently represent a C1-5 alkyl group, and m is an integer of 1 to 3),
wherein when the number of moles of the epoxy group-containing alkoxysilane compound (1) is x and the number of moles of the alkoxysilane compound (2) is y, $0.2 \leq my/nx \leq 0.7$, and subjecting the mixture to hydrolytic condensation.

In formula (1), $R^1$ and $R^2$ represent C1-5 alkyl groups. C1-5 alkyl groups are readily available as raw materials, and have high reactivity for hydrolytic condensation when used in $OR^1$ groups. Specific examples include methyl, ethyl, propyl, isopropyl, butyl and pentyl, with no particular limitation to these. $R^1$ and $R^2$ are more preferably methyl groups or ethyl groups.

Groups $R^3$ to $R^{11}$ in formula (1), specifically, each independently represent hydrogen or a C1-6 alkyl or C3-12 trialkylsilyl group. More specific examples include hydrogen, methyl, ethyl, propyl, isopropyl, butyl, isobutyl, tert-butyl, pentyl, hexyl, trimethylsilyl, triethylsilyl and tert-butyldimethylsilyl, with no limitation to these. Due to availability of the raw materials, it is preferable that $R^3$ to $R^{11}$ are hydrogen, methyl, trimethylsilyl or tert-butyldimethylsilyl groups, and specific examples other than those where all of $R^3$ to $R^{11}$ are hydrogen include those having the following structural formulas. More preferred are hydrogen and methyl, and most preferably all of $R^3$ to $R^{11}$ are hydrogen.

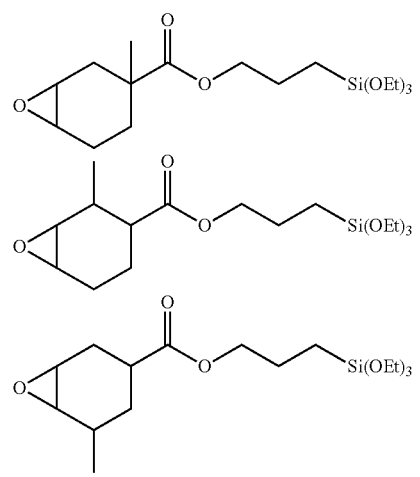

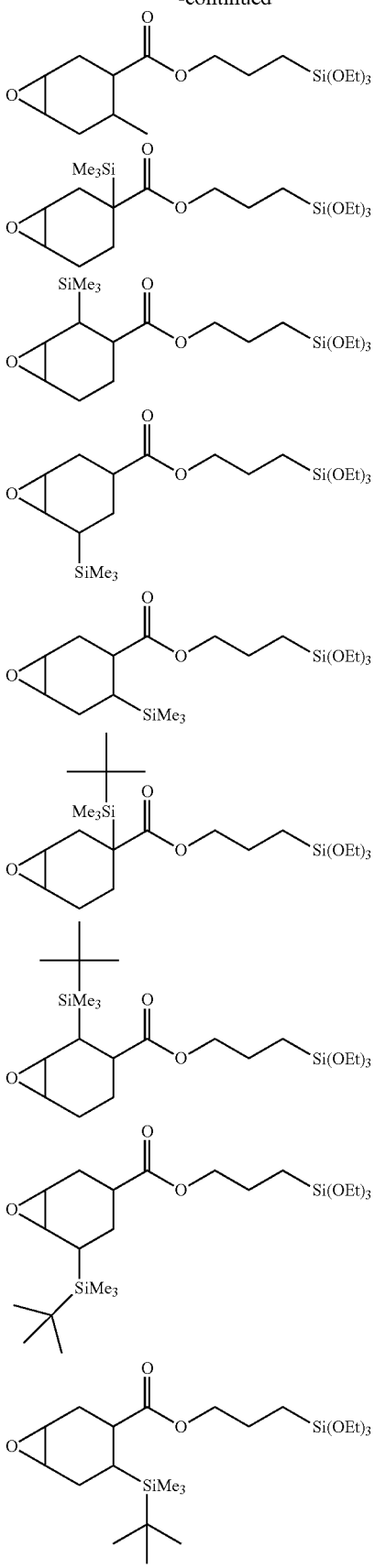

In addition, $R^5$ or $R^6$, and $R^7$ or $R^8$, may be linked together to form a ring. For example, when $R^5$ and $R^7$ are linked to form a ring, the carbon atoms to which $R^5$ and $R^7$ are respectively bonded are bonded to each other via a divalent group, such as a substituted or unsubstituted alkylene group, such that an additional ring structure is introduced into the epoxy group-containing alkoxysilane compound. Specifically, an epoxy group-containing alkoxysilane compound represented by the following formula (1') is preferred.

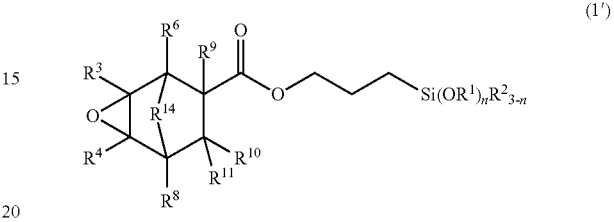

$R^1$ to $R^4$, $R^6$, $R^8$ to $R^{11}$ and n in formula (1') are the same as explained for formula (1). $R^{14}$ represents a C1-3 divalent alkylene group and preferably a methylene group, the divalent alkylene group being optionally substituted with one or more groups selected from the group consisting of C1-6 alkyl and C3-12 trialkylsilyl, on any desired carbon atom. The divalent alkylene group is preferably unsubstituted or has a methyl, trimethylsilyl or tert-butyldimethylsilyl group as a substituent, examples of which include the following structural formulas, but it is more preferably unsubstituted or has a methyl group as a substituent.

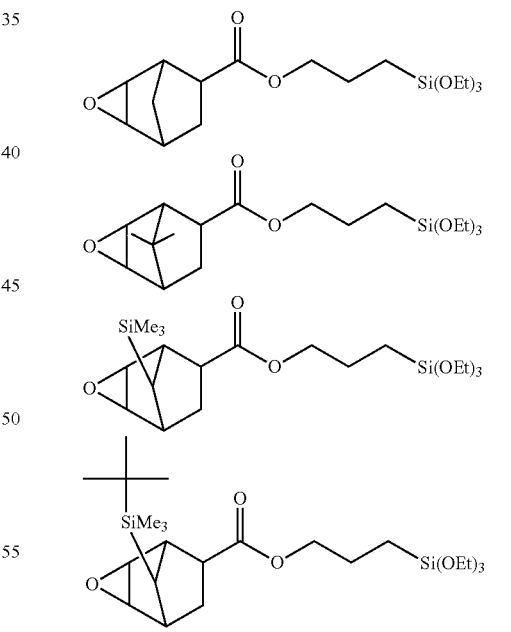

The epoxy group-containing alkoxysilane compound may be prepared by hydrosilylation reaction of an alkoxysilane compound having a Si—H bond, with an epoxy compound having an allyl group, as described in International Patent Publication No. WO2008/020637.

$R^{12}$ and $R^{13}$ in formula (2) represent C1-5 alkyl groups. Alkoxysilane compounds having C1-5 alkyl groups are readily available as raw materials, and have high reactivity for hydrolytic condensation. Specific examples include methyl, ethyl, propyl, isopropyl, butyl and pentyl, with no particular limitation to these. $R^{12}$ and $R^{13}$ are more preferably methyl groups or ethyl groups.

For preparation of the epoxysilicone condensate of the invention, the blending ratio of the epoxy group-containing alkoxysilane compound (1) and the alkoxysilane compound (2), where the number of moles of the epoxy group-containing alkoxysilane compound (1) is represented by x and the number of moles of the alkoxysilane compound (2) is represented by y, is preferably in the range of $0.2 \leq my/nx \leq 0.7$, more preferably in the range of $0.25 \leq my/nx \leq 0.65$ and even more preferably in the range of $0.3 \leq my/nx \leq 0.6$. If my/nx is too large, the proportion of silicone sites in the resin composition is too high, potentially creating problems with the gas barrier properties and Tg. If my/nx is too small, the thermal (yellowing) resistance is insufficient in many cases.

The molecular structure of the epoxysilicone condensate of the invention may be a straight-chain, cyclic, branched or three-dimensional network structure, depending on the numbers of hydrolyzable groups (n and m) in each molecule of the epoxy group-containing alkoxysilane compound (1) and alkoxysilane compound (2) used. The number of silicon atoms in each molecule is generally 2 to 200 and preferably 4 to 100. Too many silicon atoms per molecule result in increased viscosity and poor handling. Too few silicon atoms per molecule, on the other hand, can potentially result in reduced flexibility of the cured product and insufficient strength. The epoxy equivalent of the epoxysilicone condensate of the invention is generally in the range of 180 g/eq to 1000 g/eq and preferably in the range of 200 to 500 g/eq.

There are no particular restrictions on the amount of water added during preparation of the epoxysilicone condensate of the invention, but it is usually in the range of 1 to 10 mol and preferably in the range of 1.5 to 5 mol with respect to 1 mol as the total of the hydrolyzable groups in the epoxy group-containing alkoxysilane compound (1) and alkoxysilane compound (2) used as raw materials. An excessive amount of water addition may lower the solubility of the condensate in the reaction solution, potentially making it impossible to obtain the target high molecular weight product. With an excessively low amount of water addition, the hydrolytic condensation may not proceed sufficiently.

During preparation of the epoxysilicone condensate of the invention, it is preferred to use a catalyst to increase the reaction rate. There are no particular restrictions on the hydrolytic condensation catalyst used, and a known acidic catalyst or basic catalyst may be used. Examples of acidic catalysts include hydrochloric acid, nitric acid, sulfuric acid, toluenesulfonic acid, acetic acid, phosphoric acid, oxalic acid and citric acid. Examples of basic catalysts include sodium hydroxide, potassium hydroxide, cesium hydroxide, tetramethylammonium hydroxide, tetrabutylammonium hydroxide and benzyltrimethylammonium hydroxide.

There are no particular restrictions on the amount of catalyst added during preparation of the epoxysilicone condensate of the invention, but in order to obtain sufficient reactivity and restrict ring-opening of the epoxy rings and gelling, it is preferably in the range of 0.001 to 0.2 mol and more preferably in the range of 0.005 to 0.1 mol with respect to 1 mol as the total of the hydrolyzable groups in the epoxy group-containing alkoxysilane compound (1) and the alkoxysilane compound (2).

The reaction temperature for the reaction during preparation of the epoxysilicone condensate of the invention is not particularly restricted since it may differ depending on the reactivities of the epoxy group-containing alkoxysilane compound (1) and alkoxysilane compound (2) used as the raw materials, and on the solvent used, but in order to ensure a sufficiently high reaction rate and inhibit undesirable secondary reactions, it is preferably in the range of 0° C. to 100° C., and more preferably in the range of 10° C. to 80° C. An excessively low reaction temperature may not allow efficient progression of the reaction, while an excessively high reaction temperature can potentially result in progression of secondary reactions, such as ring-opening of the epoxy rings.

It is preferred to use a solvent during preparation of the epoxysilicone condensate of the invention. The solvent used is not particularly restricted so long as it uniformly dissolves the alkoxysilane raw materials and water, and as examples there may be mentioned alcohol-based solvents, such as methanol, ethanol, 2-propanol, n-butanol, isobutanol and tert-butanol, and ketone-based solvents, such as acetone, methyl ethyl ketone, diethyl ketone, methylpropyl ketone, methyl isobutyl ketone and cyclohexanone. These solvents may be used alone, or 2 or more different ones may be used in admixture.

The reaction time for the reaction during preparation of the epoxysilicone condensate of the invention is not particularly restricted since it may differ depending on the reactivities of the epoxy group-containing alkoxysilane compound (1) and alkoxysilane compound (2) used as the raw materials, and on the reaction temperature, but in order to ensure a sufficiently large molecular weight of the product, it is preferably in the range of 1 hour to 40 hours. If the reaction time is shorter than 1 hour, the unreacted raw materials or low-molecular-weight oligomers may remain, while no further condensation reaction will take place in most cases even if the reaction is extended for longer than 40 hours.

A curable composition comprising the epoxysilicone condensate described above may further comprise a curing agent or a polymerization initiator, to produce a cured product.

Addition of a curing agent will be explained first.

There are no particular restrictions on the curing agent, so long as it is known as a curing agent for epoxy resins. Examples include phenol compounds, such as phenol resins, amine compounds, such as diamine and polyamine, acid anhydrides, such as phthalic anhydride, trimellitic anhydride and pyromellitic anhydride, and poly carboxyl group-containing compounds, such as trimellitic acid, any of which compounds may be used alone, or in combinations of two or more. Among these curing agents, it is preferred to use an acid anhydride curing agent in consideration of the thermal resistance, light resistance and transparency of the obtained cured product.

There are no particular restrictions on acid anhydrides that can be used as curing agents. Examples include phthalic anhydride, trimellitic anhydride, pyromellitic anhydride, maleic anhydride, tetrahydrophthalic anhydride, methylhexahydrophthalic anhydride, methyltetrahydrophthalic anhydride, methylnadic anhydride, hydrogenated methylnadic anhydride, trialkyltetrahydrophthalic anhydride, dodecenylsuccinic anhydride, and 2,4-diethylglutaric anhydride. Preferred among these are acid anhydrides that are liquid at 25° C., such as methylhexahydrophthalic anhydride, methyltetrahydrophthalic anhydride, methylnadic anhydride, hydrogenated methylnadic anhydride, trialkyltetrahydrophthalic anhydride, dodecenylsuccinic anhydride and 2,4-diethylglutaric anhydride, with alicyclic acid anhydrides being preferred, and methylhexahydrophthalic anhydride and hydrogenated methylnadic anhydride being especially preferred. These acid anhydrides may be used alone or as mixtures of two or more, such as a mixture of 3-methylhexahydrophthalic anhydride and 4-methylhexahydrophthalic anhydride. In addition, a solid acid anhydride may be dissolved in a liquid acid anhydride for use as an acid anhydride mixture that is liquid at 25° C.

When an acid anhydride alone is to be used as the curing agent, it is used in an amount such that the ratio of the total number of acid anhydride groups with respect to the total number of epoxy groups in the composition is preferably in the range of 0.7 to 1.5 and more preferably in the range of 0.8 to 1.2. If the ratio of the total number of acid anhydride groups with respect to the total number of epoxy groups in the composition is less than 0.7, the crosslink density may be undesirably lowered. If it is greater than 1.5, the strength and humidity resistance of the cured product obtained by curing the composition tend to be undesirably impaired.

A curing accelerator may optionally be used in a curable composition comprising the epoxysilicone condensate described above. There are no particular restrictions on a curing accelerator to be used, so long as it is a compound that accelerates the reaction between the epoxy group-containing compound and the curing agent, and examples include triazine-based compounds, such as melamine, acetoguanamine, benzoguanamine and 2,4-diamino-6-vinyl-s-triazine, imidazole-based compounds, such as imidazole, 2-methylimidazole, 2-ethyl-4-methylimidazole, 2-phenylimidazole, 2-phenyl-4-methylimidazole, vinylimidazole and 1-methylimidazole, cycloamidine compounds and their derivatives, such as diazabicycloalkenes including 1,5-diazabicyclo[4.3.0]nonene-5 and 1,8-diazabicyclo[5.4.0]undecene-7, tertiary amino group-containing compounds, such as triethylenediamine, benzyldimethylamine and triethanolamine, organic phosphine compounds, such as triphenylphosphine, diphenyl (p-tolyl)phosphine, tris(alkylphenyl)phosphine and tris(alkoxyphenyl)phosphine, phosphonium salt compounds, such as ethyltriphenylphosphonium phosphate, tetrabutylphosphonium hydroxide, tetrabutylphosphonium acetate, tetrabutylphosphonium hydrogendifluoride, tetrabutylphosphonium dihydrogentrifluoride, tetraphenylphosphonium tetraphenylborate, tetraphenylphosphonium tetra-p-tolylborate, benzyltriphenylphosphonium tetraphenylborate, tetraphenylphosphonium tetrafluoroborate, p-tolyltriphenylphosphonium tetra-p-tolylborate, U-CAT5003 by San-Apro Ltd. (tetra-substituted phosphonium bromide), and dicyandiazide. These curing accelerators may be used alone or in combinations of two or more. Preferred among these curing accelerators are triazine-based compounds, organic phosphine compounds and phosphonium salt compounds.

The amount of curing accelerator added is not particularly restricted so long as a curing-accelerating effect can be obtained. However, from the viewpoint of curability of the composition of the invention and the thermal resistance and humidity resistance of the cured product obtained by curing the composition of the invention, it is preferably added in the range of 0.1 to 10 parts by mass and more preferably 1 to 7 parts by mass with respect to 100 parts by mass as the total of the epoxysilicone condensate in the composition of the invention. An additional amount of less than 0.1 part by mass may make it difficult to accomplish curing in a short period of time, while an amount of greater than 10 parts by mass may impair the thermal resistance or humidity resistance of the cured product obtained by curing the composition.

Addition of a polymerization initiator will now be explained.

A polymerization initiator to be added to the curable composition of the invention is not particularly restricted so long as it allows a cured product to be obtained from the epoxysilicone condensate. A cured product can be obtained by cationic polymerization using a cationic polymerization initiator, as with common compounds with alicyclic epoxy groups.

There are no particular restrictions on the cationic polymerization initiator to be used, so long as it is a compound that initiates ring-opening polymerization of epoxy groups. Cationic polymerization initiators are largely classified as thermal cationic polymerization initiators that produce active species upon heating and photocationic polymerization initiators that produce active species upon light irradiation. The cationic polymerization initiator for cationic polymerization of the epoxysilicone condensate described above may be either a thermal cationic polymerization initiator or a photocationic polymerization initiator, or a combination of both.

Photocationic polymerization initiators are compounds that initiate cationic polymerization of epoxy groups by irradiation with ultraviolet rays. Examples include onium salts wherein the cationic portion is sulfonium, such as triphenylsulfonium or diphenyl-4-(phenylthio)phenylsulfonium, iodonium, such as diphenyliodonium or bis(dodecylphenyl)iodonium, diazonium, such as phenyldiazonium, ammonium, such as 1-benzyl-2-cyanopyridinium or 1-(naphthylmethyl)-2-cyanopyridinium, or an Fe cation, such as (2,4-cyclopentadien-1-yl) [(1-methylethyl)benzene]-Fe, and the anionic portion is $BF_4^-$, $PF_6^-$, $SbF_6^-$ or $[BX_4^-]$ (where X is a phenyl group substituted with two or more fluorine or trifluoromethyl groups).

As thermal cationic polymerization initiators there may be used cationic or proton acid catalysts, such as triflic acid salts, boron trifluoride ether complexes or boron trifluoride, or various onium salts, such as ammonium salts, phosphonium salts and sulfonium salts.

Among such photocationic and thermal cationic polymerization initiators, onium salts are preferred for excellent balance among handling, storage stability and curability, with diazonium salts, iodonium salts, sulfonium salts and phosphonium salts being especially preferred.

There are no particular restrictions on the amount of cationic polymerization initiator used, and it may be appropriately set depending on the reactivity of the initiator, the viscosity of the epoxysilicone condensate used and the number of epoxy groups in the epoxysilicone condensate, but for most purposes it is added at 0.01 to 15 parts by mass and more preferably 0.05 to 5 parts by mass, with respect to 100 parts by mass of the epoxysilicone condensate used. An amount outside of this range is not preferred since it will result in a poor balance between the thermal resistance and humidity resistance of the cured product after cationic polymerization.

A curable composition comprising an epoxysilicone condensate of the invention may optionally contain various additives. Examples of typical additives include antioxidants to prevent oxidative degradation by heat during curing to obtain a cured product with little coloration, and ultraviolet absorbers to increase the light resistance of the cured product.

Phenol-based, sulfur-based and phosphorus-based antioxidants may be used as antioxidants, in a mixing proportion of preferably not greater than 10 parts by mass with respect to 100 parts by mass as the total amount of the epoxysilicone condensate in the composition of the invention.

Benzophenone-based, benzotriazole-based, hindered amine-based and salicylic acid-based ultraviolet absorbers may be used as ultraviolet absorbers, in a mixing proportion of preferably not greater than 10 parts by mass with respect to 100 parts by mass as the total amount of the epoxysilicone condensate in the composition of the invention.

Examples of other additives include metal oxides, such as aluminum oxide and magnesium oxide, silicon compounds, such as fine powder silica, molten silica and crystalline silica, metal hydroxides, such as aluminum hydroxide, and powdered fillers, such as kaolin, mica, quartz powder, graphite, molybdenum disulfide and glass beads. Typically, it is preferable that the mixing proportion is not greater than 100 parts by mass for powdered fillers with respect to 100 parts by mass of the epoxysilicone condensate in the composition of the invention.

A curable composition comprising an epoxysilicone condensate of the invention may be prepared by any method so long as it allows the different components to be uniformly dispersed and mixed. A common method involves thoroughly mixing prescribed amounts of the components with a mixer or the like and then melt kneading the mixture with a mixing roll or extruder, and cooling and pulverizing the mixture. As a more specific example, prescribed amounts of the components may be uniformly stirred and mixed, and then dispersed and kneaded using an apparatus, such as a planetary mixer, triple roll, twin heated roll or Raikai mixer, and finally subjected to degassing in a vacuum.

The cured product of the curable composition comprising the epoxysilicone condensate of the invention is obtained by thermosetting the curable composition, when the curable composition contains a curing agent or a thermal cationic polymerization initiator, or it is obtained by photocuring the curable composition, when the curable composition contains a photocationic polymerization initiator. There are no particular restrictions on the conditions for thermosetting the curable composition, but for most purposes a temperature of 60° C. to 150° C. and a time of 1 to 8 hours is preferred. The conditions for photocuring the curable composition are also not particularly restricted, but for most purposes, it is preferably carried out by irradiation using a low-pressure mercury lamp, high-pressure mercury lamp, ultra-high-pressure mercury lamp, deuterium lamp, metal halide lamp, halogen lamp, xenon lamp, tungsten lamp, gallium lamp, carbon arc lamp, incandescent lamp, fluorescent lamp, excimer lamp, laser or the like as the light source, with light in a wavelength range of 200 nm to 750 nm, and an irradiation dose of between 50 mJ/cm$^2$ and 2000 mJ/cm$^2$.

The cured product of the invention has excellent transparency, thermal (yellowing) resistance and gas barrier properties, and can therefore be suitably used as a raw material for an optical material, such as a plastic lens, or as an encapsulant for an optical element, such as a light emitting diode (LED), or an electronic component, such as a semiconductor chip, and useful optical elements and electronic components comprising such encapsulants may be obtained.

EXAMPLES

The present invention will now be explained in greater detail by examples, with the understanding that the invention is not limited only to the examples.

Measurement of Epoxy Equivalents

In the following examples and comparative examples, measurement of the epoxy equivalents was accomplished by the indicator titration method of JIS K7236.

Measurement of Number-Average Molecular Weight

The number-average molecular weight Mn was determined by gel permeation chromatography (GPC), with the value based on polystyrene (Reference sample: STANDARD SM-105 by Showa Denko K.K.).

The measuring conditions for GPC were as follows.
Apparatus: HPLC Unit HSS-2000 by JASCO Corp.
Column: Shodex column LF-804
Mobile phase: Tetrahydrofuran
Flow rate: 1.0 mL/min
Detector: RI-2031 Plus by JASCO Corp.
Temperature: 40.0° C.
Sample volume: 100 µl sample loop
Sample concentration: Prepared to approximately 0.1 mass %

Reference Synthesis Example 1

Synthesis of 3-(3,4-epoxycyclohexane-1-carboxylic acid)propyltriethoxysilane (Compound of formula (1) wherein n is 3, $R^1$ is ethyl and $R^3$ to $R^{11}$ are all hydrogen)

In a 1000 mL three-necked flask equipped with a dropping funnel, reflux tube and stopper there were placed 200 g (1.1 mol) of allyl 3,4-epoxycyclohexane-1-carboxylate (Showa Denko K.K.), 0.14 g of a 3% IPA solution of Pt(dvs) (3%-PT-VTS-IPA solution (divinyltetramethyldisiloxane-platinum complex isopropyl alcohol solution) by N.E. Chemcat Corp.) and 100 g of toluene (Junsei Chemical Co., Ltd.), and the interior of the three-necked flask was purged with nitrogen. After placing 270 g (1.65 mol) of triethoxysilane (Tokyo Kasei Kogyo Co., Ltd.) and 200 g of toluene in the dropping funnel, the mixture was added dropwise into the three-necked flask at 60° C. over a period of 5 hours. Upon completion of the dropwise addition, stirring was continued for another 5 hours at 60° C. The obtained reaction mixture was purified by vacuum distillation, and 120 g of 3-(3,4-epoxycyclohexane-1-carboxylic acid)propyltriethoxysilane was obtained as a colorless transparent liquid in the 150° C./0.6 Torr fraction (yield: 31%).

Example 1

Synthesis of CEA-SiO (0.50) Condensate

In a 500 mL volumetric flask equipped with a dropping funnel there were placed 100 g of 2-propanol, 35.1 g of distilled water and 1.42 g of a 25% aqueous solution of tetramethylammonium hydroxide (Showa Denko K.K.), and the mixture was uniformly mixed. Next, 30 g (86.6 mmol) of the 3-(3,4-epoxycyclohexane-1-carboxylic acid)propyltriethoxysilane obtained in Reference Synthesis Example 1, 7.81 g (65 mmol) of dimethoxydimethylsilane (compound of formula (2) wherein m is 2 and $R^{12}$ and $R^{13}$ are both methyl groups) (Tokyo Kasei Kogyo Co., Ltd.) and 50 g of 2-propanol (Junsei Chemical Co., Ltd.) were placed in the dropping funnel, and the mixture was added dropwise to the volumetric flask over a period of 20 minutes at room temperature. Upon completion of the dropwise addition, the mixture was stirred for another 9 hours at room temperature and allowed to stand for 12 hours. After then adding 150 g of distilled water and 47 g of a 0.5% aqueous solution of acetic acid to the obtained reaction mixture, the 2-propanol solvent was distilled off. The liquid in the flask was extracted with 150 g of toluene. The obtained organic layer was rinsed with water and dried using anhydrous sodium sulfate (Junsei Chemical Co., Ltd.). After filtering out the inorganic salt (sodium sulfate) and distilling off the solvent, a vacuum pump was used for drying to obtain 23.4 g of a colorless transparent liquid. FIG. 1 shows the $^1$H-NMR spectrum for the product. The peak located near 0.6 ppm is due to the two hydrogens of methylene adjacent to the silicon atom in formula (1), and the peak located near 0.1 ppm is due to the six hydrogens of the two methyl groups adjacent to the silicon atom in formula (2). The ratio my/nx calculated as the peak area ratio of these two was 0.49, which was nearly the charging ratio of 0.50. The epoxy equivalent value of the obtained reaction mixture (hereunder referred to as "CEA-SiO (0.50) condensate") was 332.35, and GPC analysis resulted in a number-average molecular weight of 1653 and a weight-average molecular weight of 1971. The average number of silicon atoms per molecule was 9, as calculated from the number-average molecular weight.

Example 2

Synthesis of CEA-SiO (0.33) Condensate

Figure 2:
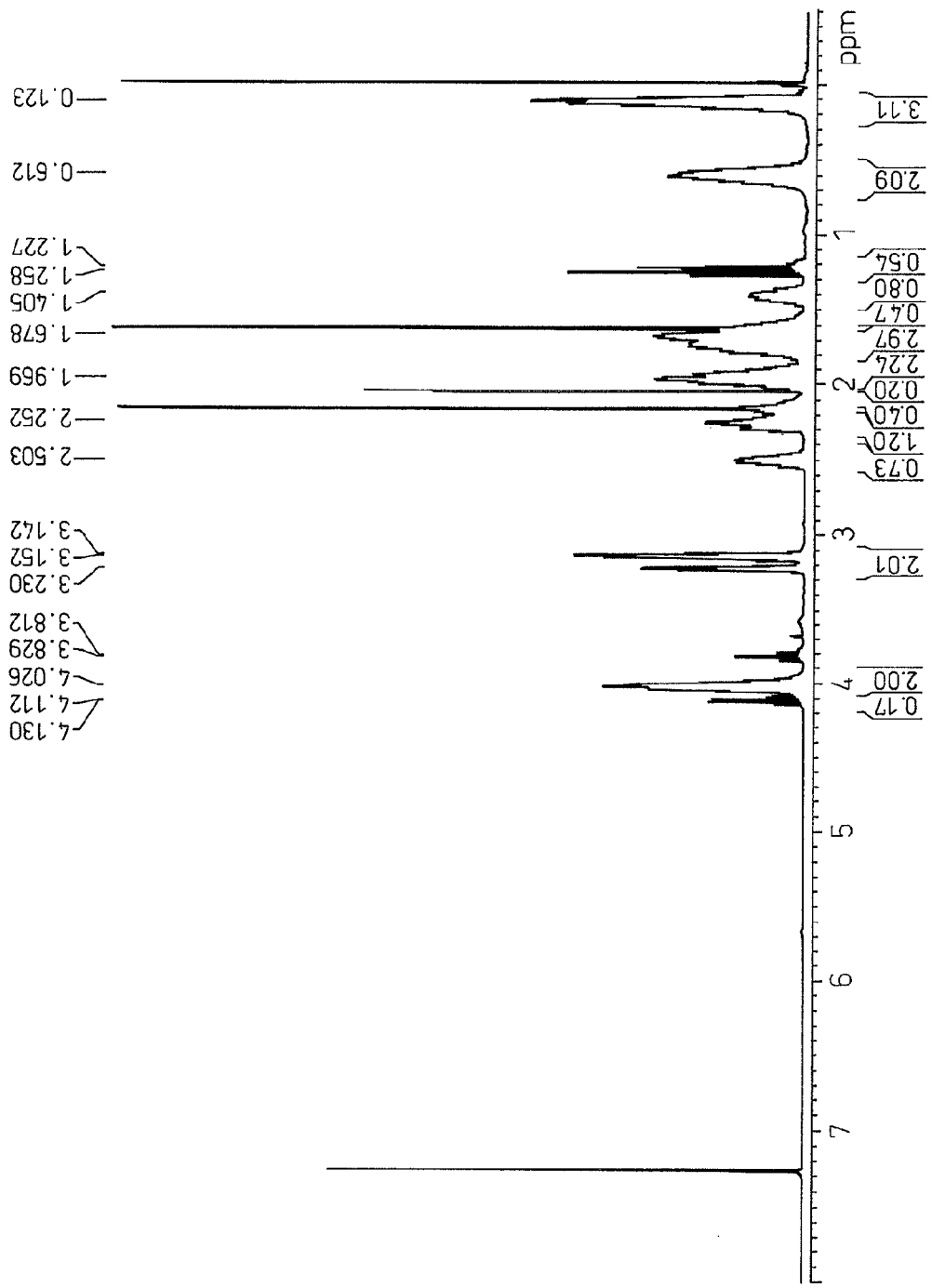
FIG. 2 shows an ¹H-NMR spectrum for the epoxysilicone condensate obtained in Example 2.

In a 100 mL volumetric flask equipped with a dropping funnel there were placed 10 g of 2-propanol, 2.07 g of distilled water and 0.21 g of a 25% aqueous solution of tetramethylammonium hydroxide (Showa Denko K.K.), and the mixture was uniformly mixed. After placing 5 g (14.4 mmol) of 3-(3,4-epoxycyclohexane-1-carboxylic acid)propyltriethoxysilane, 0.87 g (7.2 mmol) of dimethoxydimethylsilane and 5 g of 2-propanol in the dropping funnel, the mixture was added dropwise into the volumetric flask over a period of 10 minutes at room temperature. Upon completion of the dropwise addition, the mixture was stirred for another 9 hours at room temperature and allowed to stand for 12 hours. After then adding 20 g of distilled water to the obtained reaction mixture, the 2-propanol solvent was distilled off. The liquid in the flask was extracted with 20 g of toluene. The obtained organic layer was rinsed with water and dried using anhydrous sodium sulfate. After filtering out the inorganic salt (sodium sulfate) and distilling off the solvent, a vacuum pump was used for drying to obtain 3.2 g of a colorless transparent liquid. FIG. 2 shows the $^1$H-NMR spectrum for the product. The ratio my/nx calculated in the same manner as Example 1 was 0.33, which was equal to the charging ratio of 0.33. The epoxy equivalent value of the obtained reaction mixture (hereunder referred to as "CEA-SiO (0.33) condensate") was 304.23, and GPC analysis resulted in a number-average molecular weight of 2176 and a weight-average molecular weight of 3045. The average number of silicon atoms per molecule was 11, as calculated from the number-average molecular weight.

Example 3

Synthesis of CEA-SiO (0.67) Condensate

Figure 3:
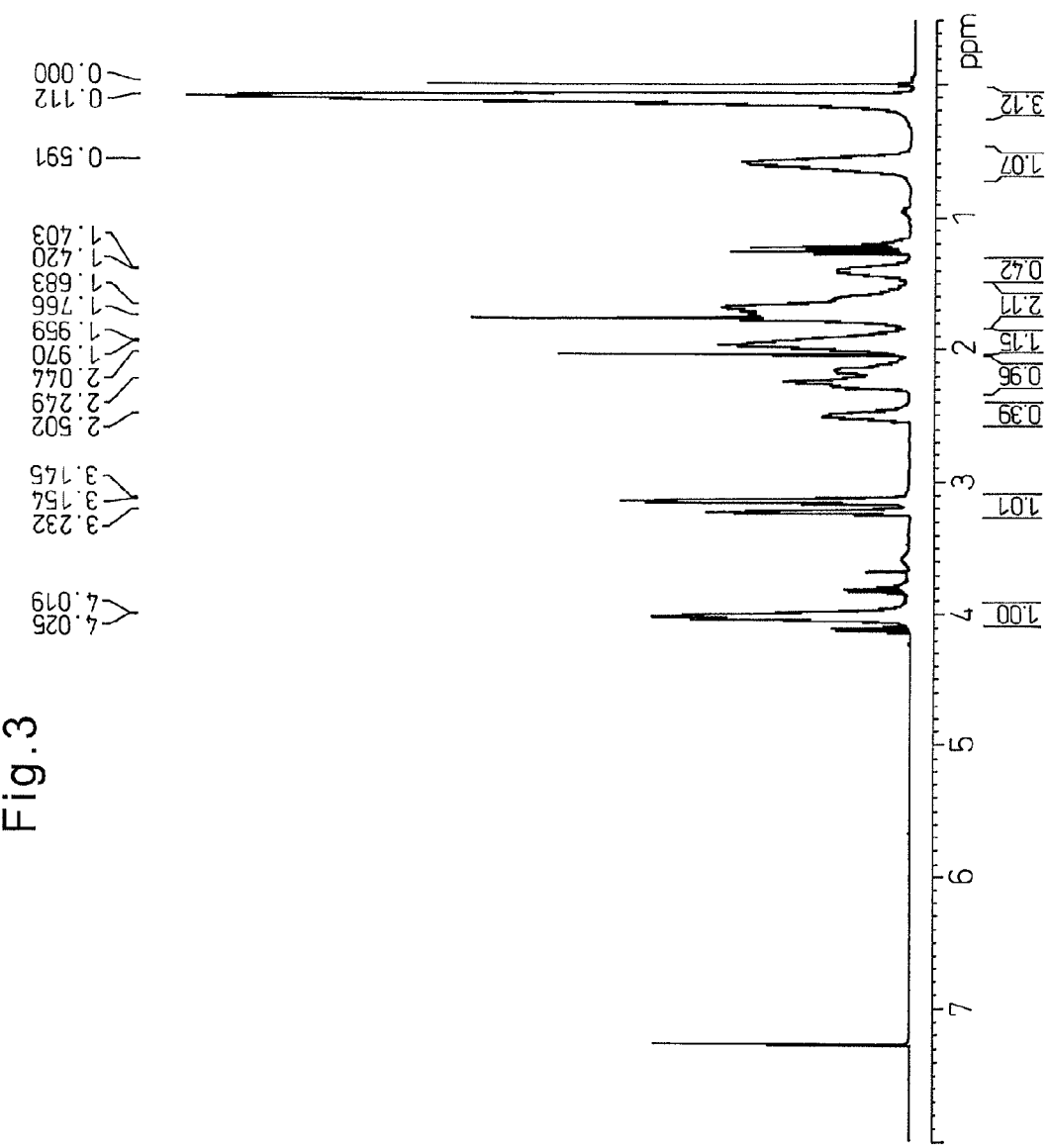
FIG. 3 shows an ¹H-NMR spectrum for the epoxysilicone condensate obtained in Example 3.

In a 100 mL volumetric flask equipped with a dropping funnel there were placed 10 g of 2-propanol, 2.6 g of distilled water and 0.26 g of a 25% aqueous solution of tetramethylammonium hydroxide (Showa Denko K.K.), and the mixture was uniformly mixed. After placing 5 g (14.4 mmol) of 3-(3,4-epoxycyclohexane-1-carboxylic acid)propyltriethoxysilane, 1.73 g (14.4 mmol) of dimethoxydimethylsilane and 5 g of 2-propanol in the dropping funnel, the mixture was added dropwise into the volumetric flask over a period of 20 minutes at room temperature. Upon completion of the dropwise addition, the mixture was stirred for another 8 hours at room temperature and allowed to stand for 12 hours. After then adding 20 g of distilled water to the obtained reaction mixture, the 2-propanol solvent was distilled off. The liquid in the flask was extracted with 20 g of toluene. The obtained organic layer was rinsed with water and dried using anhydrous sodium sulfate. After filtering out the inorganic salt (sodium sulfate) and distilling off the solvent, a vacuum pump was used for drying to obtain 3.5 g of a colorless transparent liquid. FIG. 3 shows the $^1$H-NMR spectrum for the product. The ratio my/nx calculated in the same manner as Example 1 was 0.65, which was almost equivalent to the charging ratio of 0.67. The epoxy equivalent value of the obtained reaction mixture (hereunder referred to as "CEA-SiO (0.67) condensate") was 324.33, and GPC analysis resulted in a number-average molecular weight of 1925 and a weight-average molecular weight of 3220. The average number of silicon atoms per molecule was 12, as calculated from the number-average molecular weight.

Example 4

Synthesis of CEA-SiO (0.30) Condensate

Figure 4:
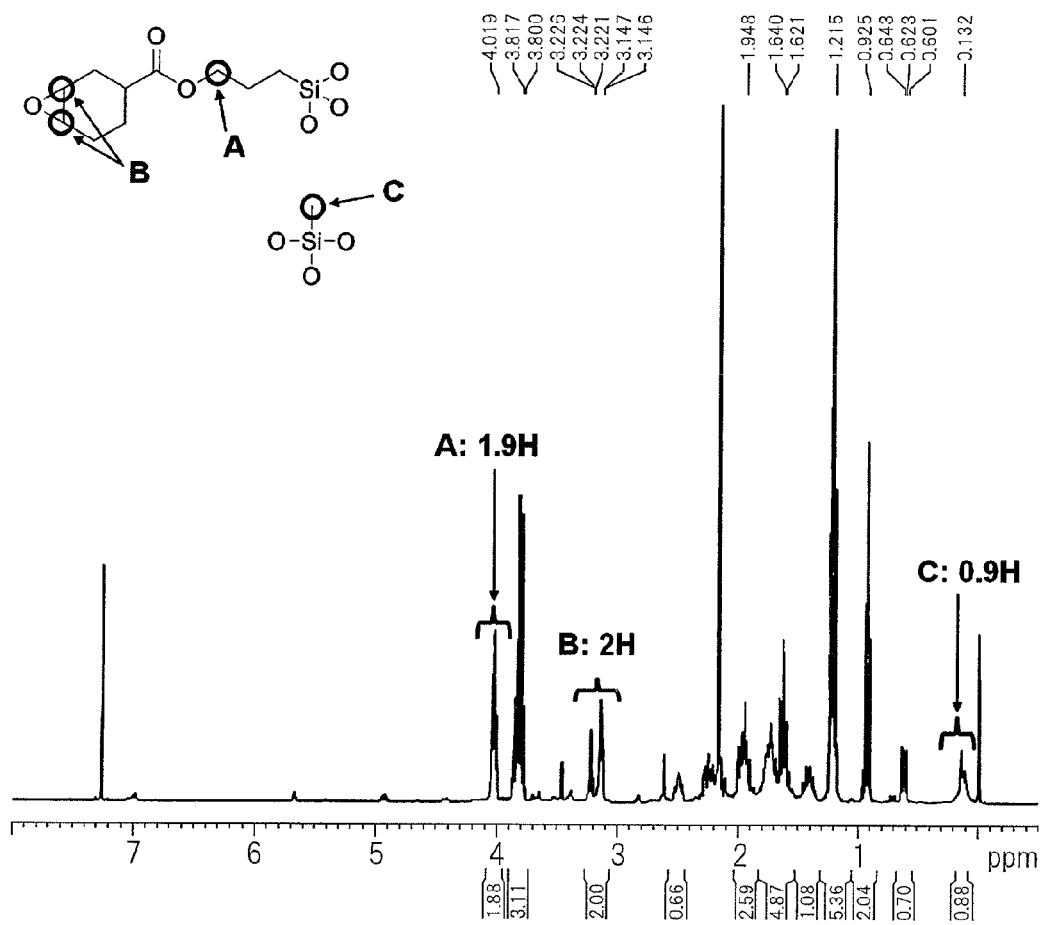
FIG. 4 shows an ¹H-NMR spectrum for the epoxysilicone condensate obtained in Example 4.

In a 100 mL volumetric flask equipped with a dropping funnel there were placed 20 g of acetone, 1.3 g of distilled water and 0.05 g of a 25% aqueous solution of tetramethylammonium hydroxide (Showa Denko K.K.), and the mixture was uniformly mixed. Next, 5 g (14.4 mmol) of 3-(3,4-epoxycyclohexane-1-carboxylic acid)propyltriethoxysilane, 0.59 g (4.3 mmol) of trimethoxymethylsilane (compound of formula (2) wherein m is 3 and $R^{12}$ and $R^{13}$ are both methyl groups) (Tokyo Kasei Kogyo Co., Ltd.) and 10 g of acetone were placed in the dropping funnel, and the mixture was added dropwise to the volumetric flask over a period of 10 minutes at room temperature. Upon completion of the dropwise addition, the mixture was stirred for another 8 hours at room temperature and allowed to stand for 12 hours. After then adding 20 g of distilled water to the obtained reaction mixture, the acetone solvent was distilled off. The liquid in the flask was extracted with 20 g of ethyl acetate. The obtained organic layer was rinsed with water and dried using anhydrous sodium sulfate. After filtering out the inorganic salt (sodium sulfate) and distilling off the solvent, a vacuum pump was used for drying to obtain 4.0 g of a colorless transparent liquid. FIG. 4 shows the $^1$H-NMR spectrum for the product. The peak located near 3.2 ppm is due to the two hydrogens (B) bonded to the two carbon atoms forming the oxirane ring in formula (1), and the peak located near 0.1 ppm is due to the three hydrogens (C) of the single methyl group adjacent to the silicon atom in formula (2). The ratio my/nx calculated as the peak area ratio of these two was 0.29, which was almost equivalent to the charging ratio of 0.30. The epoxy equivalent value of the obtained reaction mixture (hereunder referred to as "CEA-SiO (0.30) condensate") was 363.25, and GPC analysis resulted in a number-average molecular weight of 1895 and a weight-average molecular weight of 3014. The average number of silicon atoms per molecule was 6, as calculated from the number-average molecular weight.

Comparative Example 1

Synthesis of CEA-SiO (0.00) Condensate

In a 100 mL volumetric flask equipped with a dropping funnel there were placed 10 g of 2-propanol, 1.56 g of distilled water and 0.16 g of a 25% aqueous solution of tetramethylammonium hydroxide (Showa Denko K.K.), and the mixture was uniformly mixed. After placing 5 g (14.4 mmol) of 3-(3,4-epoxycyclohexane-1-carboxylic acid)propyltriethoxysilane and 5 g of 2-propanol in the dropping funnel, the mixture was added dropwise into the volumetric flask over a period of 20 minutes at room temperature. Upon completion of the dropwise addition, the mixture was stirred for another 8 hours at room temperature and allowed to stand for 12 hours. After then adding 20 g of distilled water to the obtained reaction mixture, the 2-propanol solvent was distilled off. The liquid in the flask was extracted with 20 g of toluene. The obtained organic layer was rinsed with water and dried using anhydrous sodium sulfate. After filtering out the inorganic salt (sodium sulfate) and distilling off the solvent, a vacuum pump was used for drying to obtain 2.6 g of a colorless transparent liquid. In this comparative example, the ratio my/nx was 0. The epoxy equivalent value of the obtained reaction mixture (hereunder referred to as "CEA-SiO (0.00) condensate") was 271.05, and GPC analysis resulted in a number-average molecular weight of 2817 and a weight-average molecular weight of 3803. The average number of silicon atoms per molecule was 11, as calculated from the number-average molecular weight.

Comparative Example 2

Synthesis of CEA-SiO (0.17) Condensate

In a 100 mL volumetric flask equipped with a dropping funnel there were placed 10 g of 2-propanol, 1.8 g of distilled water and 0.18 g of a 25% aqueous solution of tetramethylammonium hydroxide (Showa Denko K.K.), and the mixture was uniformly mixed. After placing 5 g (14.4 mmol) of 3-(3,4-epoxycyclohexane-1-carboxylic acid)propyltriethoxysilane, 0.43 g (3.6 mmol) of dimethoxydimethylsilane and 5 g of 2-propanol in the dropping funnel, the mixture was added dropwise into the volumetric flask over a period of 10 minutes at room temperature. Upon completion of the dropwise addition, the mixture was stirred for another 9 hours at room temperature and allowed to stand for 12 hours. After then adding 20 g of distilled water to the obtained reaction mixture, the 2-propanol solvent was distilled off. The liquid in the flask was extracted with 20 g of toluene. The obtained organic layer was rinsed with water and dried using anhydrous sodium sulfate. After filtering out the inorganic salt (sodium sulfate) and distilling off the solvent, a vacuum pump was used for drying to obtain 3.0 g of a colorless transparent liquid. The ratio my/nx was 0.17, as calculated from the charging ratio. The epoxy equivalent value of the obtained reaction mixture (hereunder referred to as "CEA-SiO (0.17) condensate") was 309.75, and GPC analysis resulted in a number-average molecular weight of 2005 and a weight-average molecular weight of 2378. The average number of silicon atoms per molecule was 9, as calculated from the number-average molecular weight.

Comparative Example 3

Synthesis of CEA-SiO (1.00) Condensate

In a 100 mL volumetric flask equipped with a dropping funnel there were placed 30 g of 2-propanol, 7.79 g of distilled water and 0.31 g of a 25% aqueous solution of tetramethylammonium hydroxide (Showa Denko K.K.), and the mixture was uniformly mixed. After placing 5 g (14.4 mmol) of 3-(3,4-epoxycyclohexane-1-carboxylic acid)propyltriethoxysilane, 2.6 g (21.6 mmol) of dimethoxydimethylsilane and 10 g of 2-propanol in the dropping funnel, the mixture was added dropwise into the volumetric flask over a period of 20 minutes at room temperature. Upon completion of the dropwise addition, the mixture was stirred for another 8 hours at room temperature and allowed to stand for 12 hours. After then adding 20 g of distilled water to the obtained reaction mixture, the 2-propanol solvent was distilled off. The liquid in the flask was extracted with 20 g of toluene. The obtained organic layer was rinsed with water and dried using anhydrous sodium sulfate. After filtering out the inorganic salt (sodium sulfate) and distilling off the solvent, a vacuum pump was used for drying to obtain 3.9 g of a colorless transparent liquid. The ratio my/nx was 1.00, as calculated from the charging ratio. The epoxy equivalent value of the obtained reaction mixture (hereunder referred to as "CEA-SiO (1.00) condensate") was 358.15, and GPC analysis resulted in a number-average molecular weight of 1990 and a weight-average molecular weight of 3458. The average number of silicon atoms per molecule was 14, as calculated from the number-average molecular weight.

Comparative Example 4

Synthesis of CEA-SiO (2.00) Condensate

In a 100 mL volumetric flask equipped with a dropping funnel there were placed 30 g of 2-propanol, 9.33 g of distilled water and 0.38 g of a 25% aqueous solution of tetramethylammonium hydroxide (Showa Denko K.K.), and the mixture was uniformly mixed. After placing 4 g (11.5 mmol) of 3-(3,4-epoxycyclohexane-1-carboxylic acid)propyltriethoxysilane, 4.16 g (34.6 mmol) of dimethoxydimethylsilane and 10 g of 2-propanol in the dropping funnel, the mixture was added dropwise into the volumetric flask over a period of 20 minutes at room temperature. Upon completion of the dropwise addition, the mixture was stirred for another 8 hours at room temperature and allowed to stand for 12 hours. After then adding 30 g of distilled water to the obtained reaction mixture, the 2-propanol solvent was distilled off. The liquid in the flask was extracted with 30 g of toluene. The obtained organic layer was rinsed with water and dried using anhydrous sodium sulfate. After filtering out the inorganic salt (sodium sulfate) and distilling off the solvent, a vacuum pump was used for drying to obtain 3.6 g of a colorless transparent liquid. The ratio my/nx was 2.00, as calculated from the charging ratio. The epoxy equivalent value of the obtained reaction mixture (hereunder referred to as "CEA-SiO (2.00) condensate") was 503.64, and GPC analysis resulted in a number-average molecular weight of 942 and a weight-average molecular weight of 1569. The average number of silicon atoms per molecule was 9, as calculated from the number-average molecular weight.

Comparative Example 5

Synthesis of CEA-SiO (3.00) Condensate

In a 100 mL volumetric flask equipped with a dropping funnel there were placed 30 g of 2-propanol, 9.34 g of distilled water and 0.38 g of a 25% aqueous solution of tetramethylammonium hydroxide (Showa Denko K.K.), and the mixture was uniformly mixed. After placing 3 g (8.6 mmol) of 3-(3,4-epoxycyclohexane-1-carboxylic acid)propyltriethoxysilane, 4.68 g (39 mmol) of dimethoxydimethylsilane and 10 g of 2-propanol in the dropping funnel, the mixture was added dropwise into the volumetric flask over a period of 20 minutes at room temperature. Upon completion of the dropwise addition, the mixture was stirred for another 7 hours at room temperature and allowed to stand for 12 hours. After then adding 30 g of distilled water to the obtained reaction mixture, the 2-propanol solvent was distilled off. The liquid in the flask was extracted with 30 g of toluene. The obtained organic layer was rinsed with water and dried using anhydrous sodium sulfate. After filtering out the inorganic salt and distilling off the solvent, a vacuum pump was used for drying to obtain 2.8 g of a colorless transparent liquid. The ratio my/nx was 3.00, as calculated from the charging ratio. The epoxy equivalent value of the obtained reaction mixture (hereunder referred to as "CEA-SiO (3.00) condensate") was 565.68, and GPC analysis resulted in a number-average molecular weight of 904 and a weight-average molecular weight of 1577. The average number of silicon atoms per molecule was 9, as calculated from the number-average molecular weight.

Preparation of Cured Product

Example 5

Preparation of CEA-SiO (0.50) Resin

A curable composition was prepared by uniformly mixing 71 parts by mass of the CEA-SiO (0.50) condensate obtained in Example 1 with 28 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Example 6

Preparation of CEA-SiO (0.33) Resin

A curable composition was prepared by uniformly mixing 66 parts by mass of the CEA-SiO (0.33) condensate obtained in Example 2 with 33 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Example 7

Preparation of CEA-SiO (0.67) Resin

A curable composition was prepared by uniformly mixing 67 parts by mass of the CEA-SiO (0.67) condensate obtained in Example 3 with 32 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Example 8

Preparation of CEA-SiO (0.30) Resin

A curable composition was prepared by uniformly mixing 71 parts by mass of the CEA-SiO (0.30) condensate obtained in Example 4 with 28 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a faint yellow transparent cured sheet with a thickness of approximately 1 mm.

Comparative Example 6

Preparation of CEA-SiO (0.00) Resin

A curable composition was prepared by uniformly mixing 63 parts by mass of the CEA-SiO (0.00) condensate obtained in Comparative Example 1 with 36 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Comparative Example 7

Preparation of CEA-SiO (0.17) Resin

A curable composition was prepared by uniformly mixing 66 parts by mass of the CEA-SiO (0.17) condensate obtained in Comparative Example 2 with 33 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Comparative Example 8

Preparation of CEA-SiO (1.00) Resin

A curable composition was prepared by uniformly mixing 70 parts by mass of the CEA-SiO (1.00) condensate obtained in Comparative Example 3 with 29 parts by mass of methylhexahydrophthalic anhydride (HN-5500E by Hitachi Chemical Co., Ltd.) as a curing agent and 1 part by mass of tetra-substituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Comparative Example 9

Preparation of CEA-SiO (2.00) Resin

A curable composition was prepared by uniformly mixing 76 parts by mass of the CEA-SiO (2.00) condensate obtained in Comparative Example 4 with 23 parts by mass of methylhexahydrophthalic anhydride (HN-5500E by Hitachi Chemical Co., Ltd.) as a curing agent and 1 part by mass of tetra-substituted phosphonium bromide (U-CAT5003 by San- Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Comparative Example 10

Preparation of CEA-SiO (3.00) Resin

A curable composition was prepared by uniformly mixing 78 parts by mass of the CEA-SiO (3.00) condensate obtained in Comparative Example 5 with 21 parts by mass of methylhexahydrophthalic anhydride (HN-5500E by Hitachi Chemical Co., Ltd.) as a curing agent and 1 part by mass of tetrasubstituted phosphonium bromide (U-CAT5003 by San-Apro Ltd.) as a curing accelerator. The curable composition was poured onto a TPX (methylpentene, by Mitsui Chemicals, Inc.) resin dish and heated with a temperature profile of 60° C./1 hour, 100° C./2 hours, and 150° C./2 hours, to obtain a colorless transparent cured sheet with a thickness of approximately 1 mm.

Comparative Example 11

Preparation of Alicyclic Epoxy Resin

A curable composition was prepared by uniformly mixing 46 parts by mass of 3,4-epoxycyclohexenylmethyl-3',4'-epoxycyclohexene carboxylate (CELLOXIDE 2021P by Daicel Chemical Industries, Ltd.) with 53 parts by mass of methylhexahydrophthalic anhydride (HN-5500E by Hitachi Chemical Co., Ltd.) as a curing agent and 1 part by mass of tetrasubstituted phosphonium bromide (U-CAT5003 by San-Apro Ltd.) as a curing accelerator. The curable composition was poured onto aluminum plates sandwiching a 1 mm-thick silicone rubber band and heated with a temperature profile of 60° C./1 hour, 100° C./2 hours, and 150° C./2 hours, to obtain a colorless transparent cured sheet with a thickness of approximately 1 mm.

Comparative Example 12

Preparation of Dimethylsilicone Resin

A curable composition was prepared by uniformly mixing 50 parts by mass of LPS-3412A (product of Shin-Etsu Chemical Co., Ltd.) and 50 parts by mass of LPS-3412B (product of Shin-Etsu Chemical Co., Ltd.). The curable composition was poured onto a TPX (methylpentene, by Mitsui Chemicals, Inc.) resin dish and heated with a temperature profile of 60° C./1 hour, 70° C./1 hour, 80° C./1 hour, 90° C./1 hour, 120° C./1 hour, and 150° C./1 hour, to obtain a colorless transparent cured sheet with a thickness of approximately 1 mm.

Measurement of Color Tone

The cured sheets with thicknesses of approximately 1 mm, obtained in Examples 5 to 8 and Comparative Examples 6 to 12, were each used to determine the color values "L", "a" and "b" with a color measurement colorimeter (ZE-2000 by Nippon Denshoku Industries Co., Ltd.) in transparent mode.

Measurement of Moisture Permeability

The cured sheets with thicknesses of approximately 1 mm obtained in Examples 5 to 8 and Comparative Examples 6 to 12 were used for actual measurement of the thickness, and then measurement of the moisture permeability [$g/m^2 \cdot 24$ hr] at 40° C., 1 atmosphere with a gas permeability measuring apparatus (GTR-30×ASD by GTR Tec Corp.).

Measurement of Oxygen Permeability

The cured sheets with thicknesses of approximately 1 mm obtained in Examples 5 to 8 and Comparative Examples 6 to 12 were used for actual measurement of the thickness, and then measurement of the oxygen permeability [$cc/m^2 \cdot 24$ hr·atm] at 40° C. with a gas permeability measuring apparatus (GTR-30×ASD by GTR Tec Corp.).

Measurement of Thermal Resistance

The cured sheets with thicknesses of approximately 1 mm, obtained in Examples 5 to 8 and Comparative Examples 6 to 12, were each used to measure the color values "L", "a" and "b" with a color measurement colorimeter (ZE-2000 by Nippon Denshoku Industries Co., Ltd.) in transparent mode. The cured product was then placed in a rotating gear-equipped oven at 150° C. and heated for 100 hours, after which the color values "L", "a" and "b" of the cured product were measured. The color difference ΔE before and after heating was determined.

Table 1 shows a summary of the values measured using the cured sheets obtained in Examples 5 to 8 and Comparative Examples 6 to 12.

TABLE 1

| | Resin name | Hunter color values | | | Moisture permeability [$g/m^2$ * 24 hr] | Oxygen permeability [$cc/m^2$ * 24 hr * atm] | ΔE |
| --- | --- | --- | --- | --- | --- | --- | --- |
| | | L | a | b | | | |
| Example 5 | CEA-SiO (0.50) | 93.55 | −0.09 | 1.26 | 0.26 | 164 | 4.5 |
| Example 6 | CEA-SiO (0.33) | 95.37 | −0.84 | 0.78 | 0.74 | 92 | 7.1 |
| Example 7 | CEA-SiO (0.67) | 94.85 | 0.28 | 0.22 | 0.82 | 205 | 6.5 |
| Example 8 | CEA-SiO (0.30) | 94.44 | 0.05 | 1.54 | 0.63 | 76 | 8.2 |
| Comp. Ex. 6 | CEA-SiO (0.00) | 95.95 | −0.27 | 0.71 | 0.54 | 58 | 9.4 |
| Comp. Ex. 7 | CEA-SiO (0.17) | 95.99 | 0.09 | 0.68 | 0.91 | 60 | 9.9 |
| Comp. Ex. 8 | CEA-SiO (1.0) | 95.29 | 0.42 | 0.30 | 0.58 | 490 | 9.1 |
| Comp. Ex. 9 | CEA-SiO (2.0) | 95.39 | −0.05 | 0.77 | 2.35 | 932 | 16.3 |

TABLE 1-continued

|  | Resin name | Hunter color values | | | Moisture permeability [g/m² * 24 hr] | Oxygen permeability [cc/m² * 24 hr * atm] | ΔE |
|---|---|---|---|---|---|---|---|
|  |  | L | a | b |  |  |  |
| Comp. Ex. 10 | CEA-SiO (3.0) | 94.98 | 0.55 | 0.10 | 3.36 | 2141 | 16.4 |
| Comp. Ex. 11 | Alicyclic epoxy resin | 95.01 | −0.12 | 0.74 | 2.06 | 81 | 5.1 |
| Comp. Ex. 12 | Dimethyl-silicone resin | 95.15 | 0.02 | 1.05 | 22.20 | 33550 | 0.2 |

The ΔE values for Examples 5 to 8 were smaller than Comparative Examples 6 to 10, indicating that cured products with excellent thermal resistance were obtained. The moisture permeability for Examples 5 to 8 was less than half of that for Comparative Example 11, while the oxygen permeability was of an equivalent level, and the resins thus had high gas barrier properties. Comparative Example 12 shows the results for similar evaluation of a dimethylsilicone resin as an example of a conventional silicone resin. The thermal resistance was satisfactory, but the moisture barrier property and oxygen barrier property were notably inferior to Examples 5 to 8. The color tones of Examples 5 to 8 were of the same level as the resins of Comparative Examples 11 and 12, which have been used as optical materials in the prior art.

INDUSTRIAL APPLICABILITY

According to the invention, it is possible to provide cured products with excellent thermal resistance and gas barrier properties, which have high potential for use in fields including encapsulants for optical elements, such as blue and white light emitting diodes, and encapsulants for electronic circuits, such as semiconductors.

The invention claimed is:

1. An epoxysilicone condensate which is the product of hydrolytic condensation of an epoxy group-containing alkoxysilane compound represented by the following formula (1):

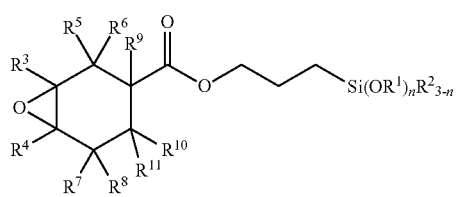

(wherein $R^1$ and $R^2$ each independently represent a C1-5 alkyl group, $R^3$ to $R^{11}$ each independently represent hydrogen or a C1-6 alkyl or C3-12 trialkylsilyl group, and n is an integer of 1 to 3, and $R^5$ or $R^6$, and $R^7$ or $R^8$, may optionally be linked together to form a ring), and an alkoxysilane compound represented by the following formula (2):

$$Si(OR^{12})_m R^{13}_{4-m} \quad (2)$$

(wherein $R^{12}$ and $R^{13}$ each independently represent a C1-5 alkyl group, and m is an integer of 1 to 3), wherein when the number of moles of the epoxy group-containing alkoxysilane compound (1) is x and the number of moles of the alkoxysilane compound (2) is y, 0.2≤my/nx≤0.7.

2. The epoxysilicone condensate according to claim 1, wherein $R^3$ to $R^{11}$ in formula (1) are all hydrogen.

3. A curable composition comprising the epoxysilicone condensate according to claim 2.

4. A cured product of the curable composition according to claim 3.

5. An optical element comprising the cured product according to claim 4 as an encapsulant.

6. An electronic component comprising the cured product according to claim 4 as an encapsulant.

7. A curable composition comprising the epoxysilicone condensate according to claim 1.

8. A cured product of the curable composition according to claim 7.

9. An optical element comprising the cured product according to claim 8 as an encapsulant.

10. An electronic component comprising the cured product according to claim 8 as an encapsulant.

* * * * *